United States Patent [19]
Song et al.

[11] Patent Number: 5,399,361
[45] Date of Patent: Mar. 21, 1995

[54] COLLAGEN-CONTAINING SPONGES AS DRUG DELIVERY COMPOSITIONS FOR PROTEINS

[75] Inventors: Suk-Zu Song, Moorpark; Andrew Morawiecki, Camarillo, both of Calif.

[73] Assignee: Amgen Inc., Thousand Oaks, Calif.

[21] Appl. No.: 268,063

[22] Filed: Jun. 28, 1994

Related U.S. Application Data

[63] Continuation of Ser. No. 877,561, May 1, 1992, abandoned.

[51] Int. Cl.$^6$ .................. A61K 31/74; A61K 9/70; A61F 13/02; A61L 15/32
[52] U.S. Cl. ........................ 424/486; 424/423; 424/443; 424/445; 424/485; 424/488; 514/801; 514/944; 514/953; 128/DIG. 8; 606/229
[58] Field of Search .............. 424/78.06, 423, 443, 424/445, 485, 486, 488; 514/801, 944, 953; 128/DIG. 8; 606/229

[56] References Cited

U.S. PATENT DOCUMENTS

| | | | |
|---|---|---|---|
| 3,157,524 | 11/1964 | Artandi | 106/22 |
| 4,292,972 | 10/1981 | Pawelchak et al. | 604/368 |
| 4,320,201 | 3/1982 | Berg | 435/265 |
| 4,412,947 | 11/1983 | Cioca | 530/356 |
| 4,453,939 | 6/1984 | Zimmerman et al. | 604/368 |
| 4,600,533 | 7/1986 | Chu | 530/356 |
| 4,642,118 | 2/1987 | Kuroyanagi et al. | 623/15 |
| 4,655,980 | 4/1987 | Chu | 264/202 |
| 4,689,399 | 8/1987 | Chu | 530/356 |
| 4,808,402 | 2/1989 | Leibovich et al. | 424/78.06 |
| 4,837,285 | 6/1989 | Berg | 530/356 |
| 4,841,962 | 6/1989 | Berg et al. | 602/50 |
| 4,937,323 | 6/1990 | Silver et al. | 530/356 |
| 4,950,699 | 8/1990 | Holman | 424/448 |

FOREIGN PATENT DOCUMENTS

| | | |
|---|---|---|
| 069260 | 1/1983 | European Pat. Off. . |
| 0167828 | 1/1984 | European Pat. Off. . |
| 0187014 | 7/1986 | European Pat. Off. . |
| 518697 | 12/1992 | European Pat. Off. . |
| 1347582 | 2/1972 | United Kingdom . |
| 8603122 | 6/1986 | WIPO . |
| 9000060 | 6/1989 | WIPO . |
| 90/13320 | 11/1990 | WIPO . |

OTHER PUBLICATIONS

Oluwasanni et al., J. Trauma 16:348–353 (1976).
Collins et al., Surg. Forum 27: 551–553 (1976).
Doillon et al., Scanning Electron Microscopy III:13-13–1320 (1984).
Doillon and Silver, Biomaterials 7:3–8 (1986).
Doillon et al., Biomaterials 8:195–200 (1987).
Abbenhaus et al., Surg. Forum 16:477–478 (1965).
Yannas and Burke, J. Biomed. Mat. Res. 14:68–81 (1980).
Chvapil et al., Int. Rev. Connect. Tissue Res. 6:1–61 (1973).
Pachence et al., Med. Device and Diag. Ind., 9:49–55 (1987).

*Primary Examiner*—Thurman K. Page
*Assistant Examiner*—Carlos Azpuru
*Attorney, Agent, or Firm*—Daniel M. Chambers; Daniel R. Curry

[57] ABSTRACT

Collagen-containing sponges comprising an absorbable gelatin sponge, collagen, and an active ingredient are disclosed as are methods of enhancing wound healing of external and internal wounds using such sponges.

13 Claims, 10 Drawing Sheets

COLLAGEN-CONTAINING SPONGES AS DRUG DELIVERY COMPOSITIONS FOR PROTEINS

This application is a continuation of application Ser. No. 07/877,561, filed May 1, 1992, now abandoned, which is hereby incorporated by reference.

BACKGROUND OF THE INVENTION

The present invention relates to collagen-containing sponges for improved sustained release delivery of pharmaceuticals.

Collagen has been used previously as a component in pharmaceutical sponges. Artandi [U.S. Pat. No. 3,157,524, issued Nov. 17, 1964], disclosed a sponge comprised of acid treated swollen collagen. Oluwasanmi et al. [J. Trauma 16:348-353 (1976)] disclosed a 1.7 millimeter thick collagen sponge that is crosslinked by glutaraldehyde. Collins et al. [Surg. Forum 27:551-553 (1976)] disclosed an acid-swollen collagen sponge that is crosslinked by glutaraldehyde. Berg et al. [U.S. Pat. No. 4,320,201, issued Mar. 16, 1982], disclosed a swollen sponge of high collagen purity produced by enzymatically degrading animal hides, digesting the mass in alkali or acid, mechanically comminuting the mass to produce specified lengths of collagen fibers, and crosslinking the fibers. Berg et al. [U.S. Pat. No. 4,837,285, issued Jun. 6, 1989], disclosed porous beads that have a collagen skeleton of 1 to 30 percent of the bead volume. These beads are useful as substrates for cell growth. Doillon et al. [Scanning Electron Microscopy III:1313-1320 (1984)], Doillon and Silver [Biomaterials 7:3-8 (1986)], and Doillon et al. [Biomaterials 8:195-200 (1987)], disclosed the growth of cells in collagen sponges with pore sizes of from about 60 to 250 μm. Some of the sponges also contained hyaluronic acid and/or fibronectin.

In addition, collagen has been used as a component in salves [PCT Patent Application WO 86/03122, published Jun. 5, 1986]. Collagen has also been used for wound healing in conjunction with electrical currents [Silver and Dunn, U.S. Pat. No. 4,937,323, issued Jun. 26, 1990].

In addition, membranes containing collagen have been used in the prior art. Abbenhaus et al., Surg. Forum 16:477-478 (1965) disclosed collagen films of 2 to 3 millimeter thickness that were produced by heating and dehydrating collagen extracted from cow hides. Chu disclosed non-chemically crosslinked collagen implants produced by compression, which are useful for sustained drug delivery [European Patent Application 187014, published Jul. 9, 1986; U.S. Pat. No. 4,600,533, issued Jul. 15, 1986; U.S. Pat. No. 4,655,980, issued Apr. 7, 1987; U.S. Pat. No. 4,689,399, issued Aug. 25, 1987; and PCT Pat. Application WO 90/00060, published Jun. 28, 1989]. Cioca [U.S. Pat. No. 4,412,947, issued Nov. 1, 1983], disclosed an essentially pure collagen sheet made by freeze drying a suspension of collagen in an organic acid. Kuroyanagai et al. [European Patent Application 167828, published Jan. 15, 1984; U.S. Pat. No. 4,642,118, issued Feb. 10, 1987], disclosed an artificial skin composed of two layers: collagen and a poly-alpha-amino acid. Berg et al. [U.S. patent application Ser. No. 4,841,962, issued Jun. 27, 1989], disclosed a wound dressing composed of three layers: an adhesive, a cross-linked collagen matrix, and a multilayer polymer film. Holman, U.S. Pat. No. 4,950,699, issued Aug. 21, 1990, disclosed a wound dressing consisting of less than 10% collagen mixed with an acrylic adhesive. Cioca et al., British Pat. No. 1,347,582, disclosed a collagenic wound dressing consisting of a freeze dried polydisperse collagen mixture.

Steffan et al., European Patent Application 069260, published Jan. 12, 1983, disclosed a collagen insert consisting of high purity native collagen. Zimmerman et al. [U.S. Pat. No. 4,453,939, issued Jun. 12, 1984], disclosed a wound healing composition containing collagen coated with fibrinogen, factor XIII fibrinigen, and/or thrombin. Leibovich et al. [U.S. Pat. No. 4,808,402, issued Feb. 1989], disclosed a composition for treating wounds comprising collagen, bioerodible polymer, and tumor necrosis factor. Yannas and Burke [J. Biomed. Mat. Res. 14:68-81 (1980)], have reviewed the design of artificial skin, some examples of which contain collagen. Chvapil et al., Int. Rev. Connect. Tissue Res. 6:1-61 (1973), particularly at pages 51 to 52; and Pachence et al., Med. Device and Diag. Ind., 9:49-55 (1987), disclose various uses of collagen, including its use as a drug delivery vehicle.

Most of the previously utilized collagen containing sponges have been used as substrates or skeletons for the growth of cells at a wound site and have not been used for the delivery of pharmaceutical agents. The present invention provides a much desired improvement in pharmaceutical sponges by providing for a steady, continuous and sustained release of therapeutic agents over an extended period of time

SUMMARY OF THE INVENTION

The present invention relates to a collagen-containing sponge comprising an absorbable gelatin sponge, collagen, and an active ingredient. Preferably, the absorbable gelatin sponge is a crosslinked gelatin.

Another aspect of the present invention relates to a collagen-containing sponge further comprising one or more of a plasticizer, a stabilizing agent, a drying enhancer or a buffer. Preferably, the plasticizer is selected from polyethylene glycol and glycerol; the stabilizing agent is a sugar selected from the group consisting of mannitol, lactose and glucose; the drying enhancer is an alcohol selected from the group consisting of ethanol, methanol and isopropyl alcohol; and the buffer is a suitable biological buffer. Preferred active ingredients are selected from the group consisting of PDGF, EGF, FGF, PDEGF, PD-ECGF, KGF, IGF-1, IGF-2, TNF, BDNF, CNTF, and NT-3.

Another aspect of the present invention relates to a method of enhancing wound healing of an epidermal wound comprising the administration of a wound healing effective amount of an active ingredient via a collagen-containing sponge according to another aspect of the present invention.

Another aspect of the present invention relates to a method of enhancing wound healing of an internal wound comprising the administration of a wound healing effective amount of an active ingredient via a collagen-containing sponge according to another aspect of the present invention.

DETAILED DESCRIPTION OF THE INVENTION

Figure 1:
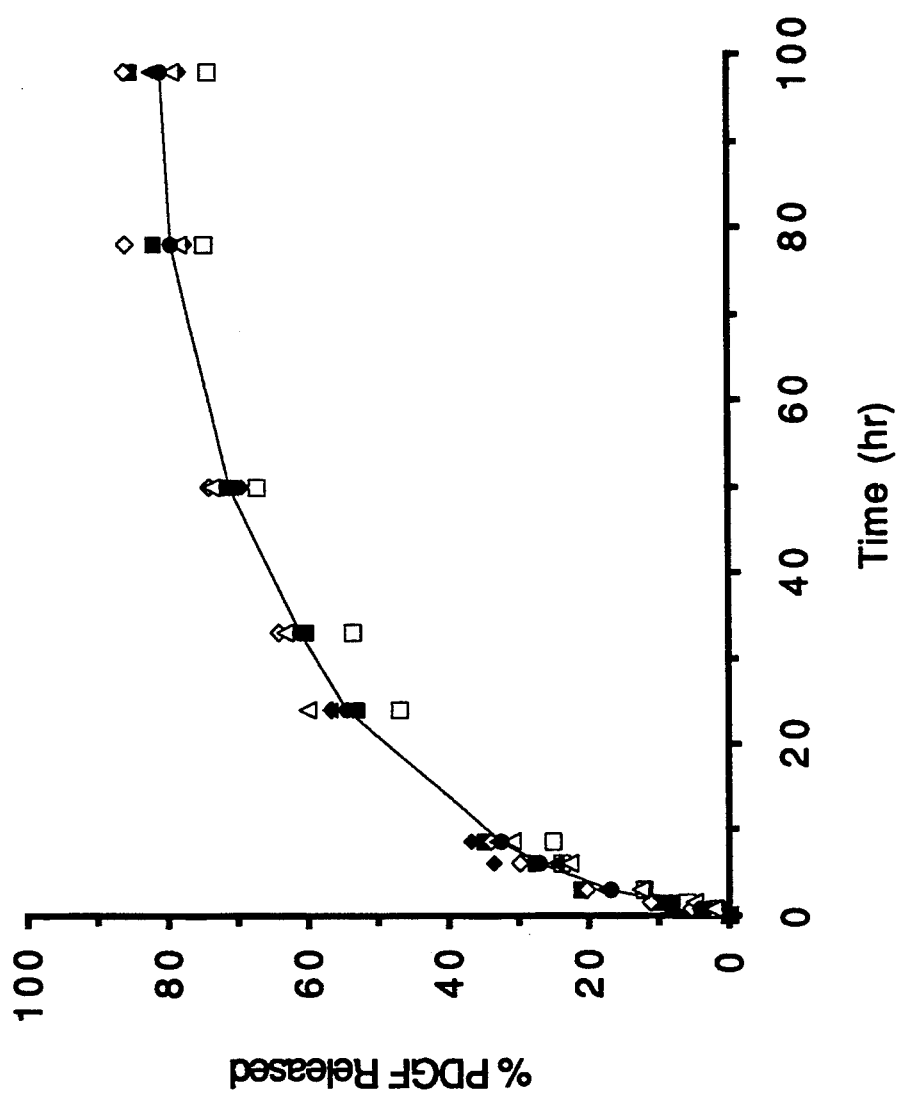
FIG. 1 shows a release profile for PDGF from a dry Gelfoam-Collagen Sponge in vitro.
Figure 2:
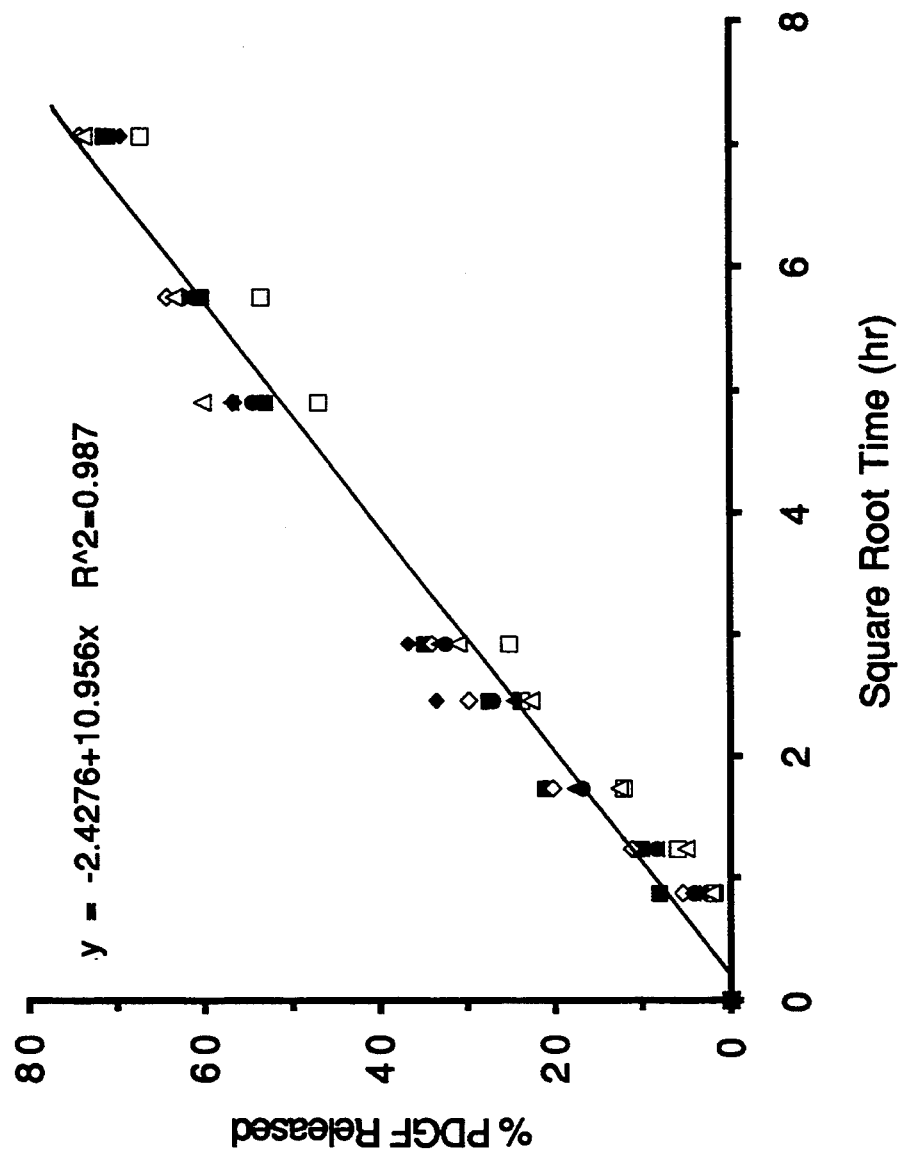
FIG. 2 shows a release profile for PDGF from a dry Gelfoam-Collagen Sponge in vitro showing first order kinetics.

The present invention relates to a collagen-containing sponge comprising an absorbable gelatin sponge, collagen, and an active ingredient.

An appropriate absorbable gelatin sponge is crosslinked gelatin, for example Gelfoam (Upjohn, Inc., Kalamzoo, Mich.). The absorbable gelatin sponge can be combined with a collagen and active ingredient by soaking the absorbable gelatin sponge in a solution comprising soluble collagen and active ingredient. Alternately, a predetermined amount of a collagen solution can be transferred on top of the gelatin sponge, and the solution can be absorbed.

Soluble collagen is collagen that has an average molecular weight of less than 400,000, preferably having a molecular weight of about 300,000. A particularly suitable soluble collagen is Semex S (Semex Medical Co., Malvern, Pa.). This particular soluble collagen is also advantageous because it is the atelopeptide form of the collagen. Atelopeptide collagen is collagen that is free of telopeptide, which is a peptide located at one end of purified collagen often associated with immunogenicity. A solution of the telopeptide form of collagen can be converted to the atelopeptide form of collagen via hydrolysis using organic acid. Another preferred characteristic of the soluble collagen is that it possesses a minimal amount of crosslinking, i.e., 0.5% or less.

The soluble collagen can be dissolved in a suitable solvent such as water to produce a solution that contains from about 0.5 to about 10% of collagen by weight, preferably from about 1 to about 5% by weight, and more preferably about 2% by weight.

A solution of soluble collagen or a dispersion of collagen fibrils in suspension is used to soak the absorbable gelatin sponge. Typically, a suitable amount of the collagen solution is transferred on top of the absorbable gelatin sponge. In another case, the collagen solution is poured into a container holding the gelatin sponge. Suitable conditions include allowing the soaked sponge to dry at a suitable temperature for a suitable period of time. Generally, the amount of drying time necessary is shorter as the drying temperature is raised. Specifically, a suitable temperature is from about 15° C. to 35° C. preferably about room temperature, and a suitable drying time is sufficient time so that the marginal loss of solvent content is essentially zero (e.g., drying time of about an hour to about 10 days, preferably about one to about five days).

To optimize desirable characteristics of a preferred collagen containing sponge, various additives may be optionally included in the collagen solution. Such desirable characteristics include flexibility, stability, accelerated drying time and a pH compatible with the active ingredient to be utilized.

To improve flexibility, a suitable plasticizer can be used. Suitable plasticizers include polyethylene glycol and glycerol, preferably glycerol. Such plasticizers can be present in an amount from zero to about 100% of the weight of collagen present, preferably from about 10 to about 30% of the weight of collagen present, most preferably about 20% of the weight of collagen present.

To improve the stability of the active ingredient, a suitable stabilizing agent can be used in the collagen. Suitable stabilizing agents include most sugars, preferably mannitol, lactose, and glucose, more preferably mannitol. Such stabilizing agents can be present in an amount from zero to about 5% of the weight of collagen present, preferably about 1% of the weight of collagen present.

To accelerate drying time for the collagen, a drying enhancer can be used. Suitable drying enhancers include alcohols, preferably ethanol, methanol and isopropyl alcohol, more preferably ethanol. Such drying enhancers can be present in an amount from zero to about 50% of the weight of the total solution or suspension, preferably from about 10 to about 30% of the weight of the total solution or suspension, more preferably about 20% of the weight of the total solution or suspension.

To produce a pH that is compatible with a particular active ingredient being used, a suitable buffer can be used in the film. Suitable buffers include most of the commonly known and utilized biological buffers, preferably acetate, phosphate and citrate, more preferably acetate and phosphate. Such buffers can be present in an amount of from about 0.01% to about 2% of the weight of the collagen solution or suspension. A compatible pH is one that maintains the stability of an active ingredient, optimizes its therapeutic effect or protects against its degradation. A suitable pH is generally from about 3 to about 8, preferably about 5 to about 8, and most preferably about neutral pH of from about 7.0 to about 7.5.

Preferred active ingredients are those biological agents which enhance wound healing or regeneration of nerve tissue, particularly recombinant proteins. Such preferred active ingredients include platelet derived growth factor (PDGF), epidermal growth factor (EGF), fibroblast growth factor (FGF), platelet derived epidermal growth factor (PDEGF), platelet derived endothelial cell growth factor (PD-ECGF) keratinocyte growth factor (KGF), insulin-like growth factors 1 and 2 (IGF-1 and IGF-2), tumor necrosis factor (TNF), brain derived neurotrophin factor (BDNF), ciliary neurotrophic factor (CNTF) and neurotrophin-3 (NT-3). A preferred active ingredient is PDGF or PD-ECGF, most preferably PDGF. Such active ingredients are present in an amount sufficient to enhance healing of a wound, i.e., a wound healing effective amount. The actual amount of the active ingredient will be determined by the attending clinician and will depend on various factors such as the severity of the wound, the condition of the patient, the age of the patient and any collateral injuries or medical ailments possessed by the patient. Generally, the amount of active ingredient will be in the range of about 1 $\mu g/cm^2$ to 5 $mg/cm^2$.

The collagen sponges of the present invention are useful as a means of delivering the active ingredient to cells or tissue with which it is in contact. For example, in the treatment of burns or other traumas to the skin, a collagen-containing sponge can be placed on the wound to deliver a suitable active ingredient to the traumatized area. PDGF is a particularly suitable active ingredient for such uses. Collagen-containing sponges can also be used to accelerate healing of surgical wounds. When used in such a way, the sponge can be placed in the surgical incision and stitched into the wound as an interface between the two surgical wound surfaces. Collagen-containing sponges can also be used to deliver neurotrophic factors. When used in such a manner, the collagen-containing sponge can be placed in direct contact with or adjacent to the nerve tissue to be treated with the neurotrophic factor.

EXAMPLES

EXAMPLE 1

Preparation of a Collagen-containing Sponge

A piece of gelatin sponge (Gelfoam ®:80×250×10 mm), was rolled out with a metal rod (diameter: 32 mm, length:130 mm), much like dough to make a thin sheet. The resulting thickness of the sheet was 1 mm. Wafers were cut out from the thin sheet with a brass punch. Wafers with a large diameter (diameter: 18 mm, weight: 1.5 mg) were cut for in vivo studies.

In one study, 0.24 ml or 0.40 ml of the collagen solution containing PDGF was pipetted on top of each wafer. In another study, the wafers were soaked in a collagen solution. The collagen solution containing PDGF was prepared as follows. First, a 4% collagen solution was prepared by dissolving 2 g of a soluble collagen (Semex S Semex, Frazer, Pa.) in 50 ml of distilled water at 30°-50° C. To 16 ml of the resulting solution, 0.13 ml of glycerol, 2 ml of alcohol, and 2 ml of a PDGF solution (2 mg/ml acetate buffer) was added. Additionally, a trace amount of $^{125}$I-PDGF were added to the solution. After the solution was absorbed by each wafer, the wafer was dried overnight to produce a sponge-collagen system containing PDGF.

EXAMPLE 2

Kinetics of Release from Collagen-containing Sponges.

Figure 3:
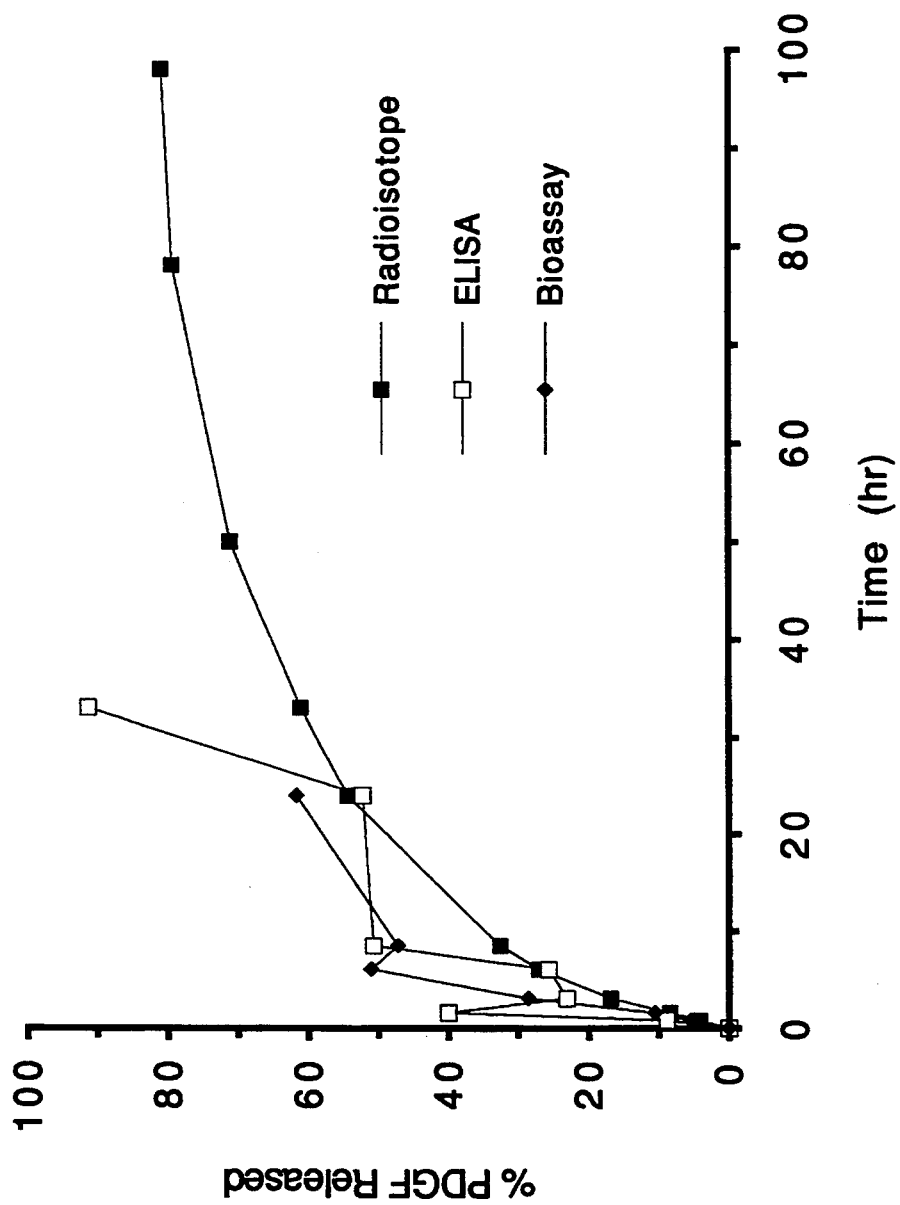
FIG. 3 shows the correlation of PDGF release as measured by radioisotope, ELISA and PDGF bioassay.
Figure 4:
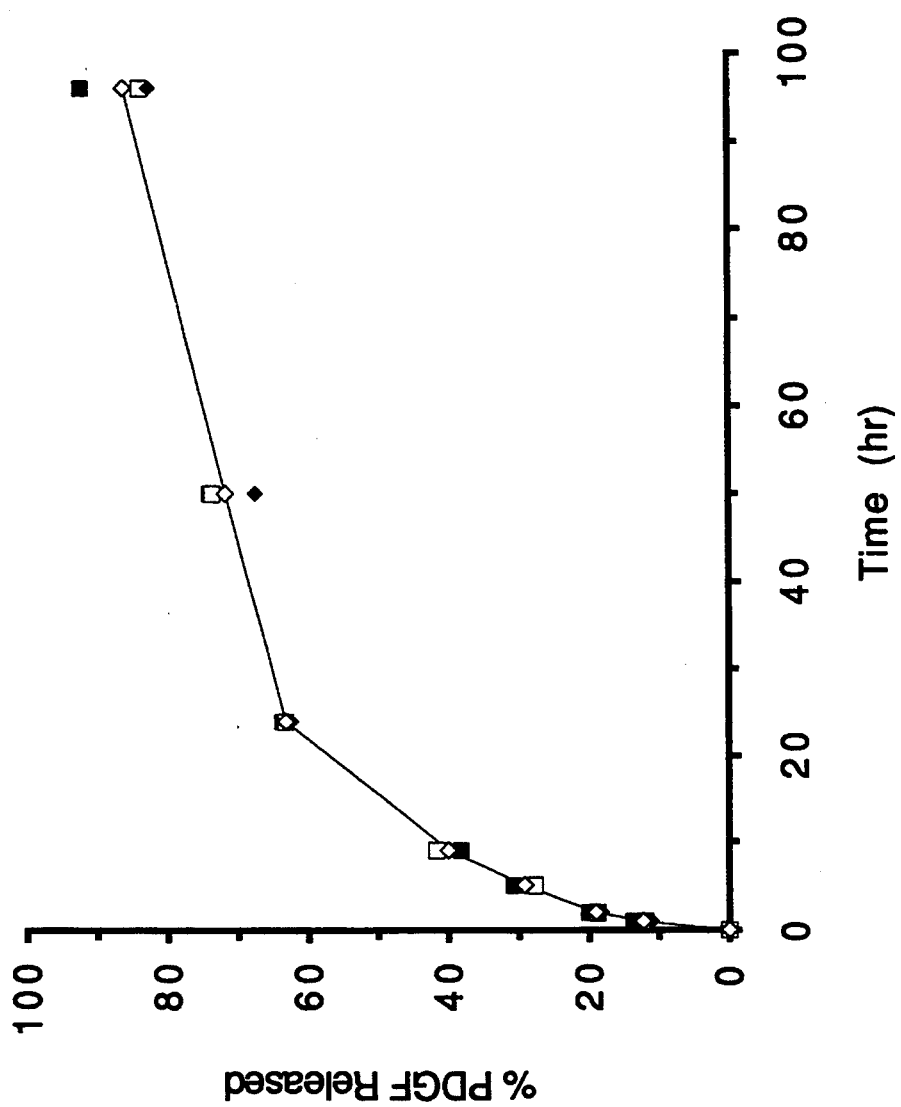
FIG. 4 shows a release profile for PDGF from a wet Gelfoam-Collagen Sponge in vitro.
Figure 5:
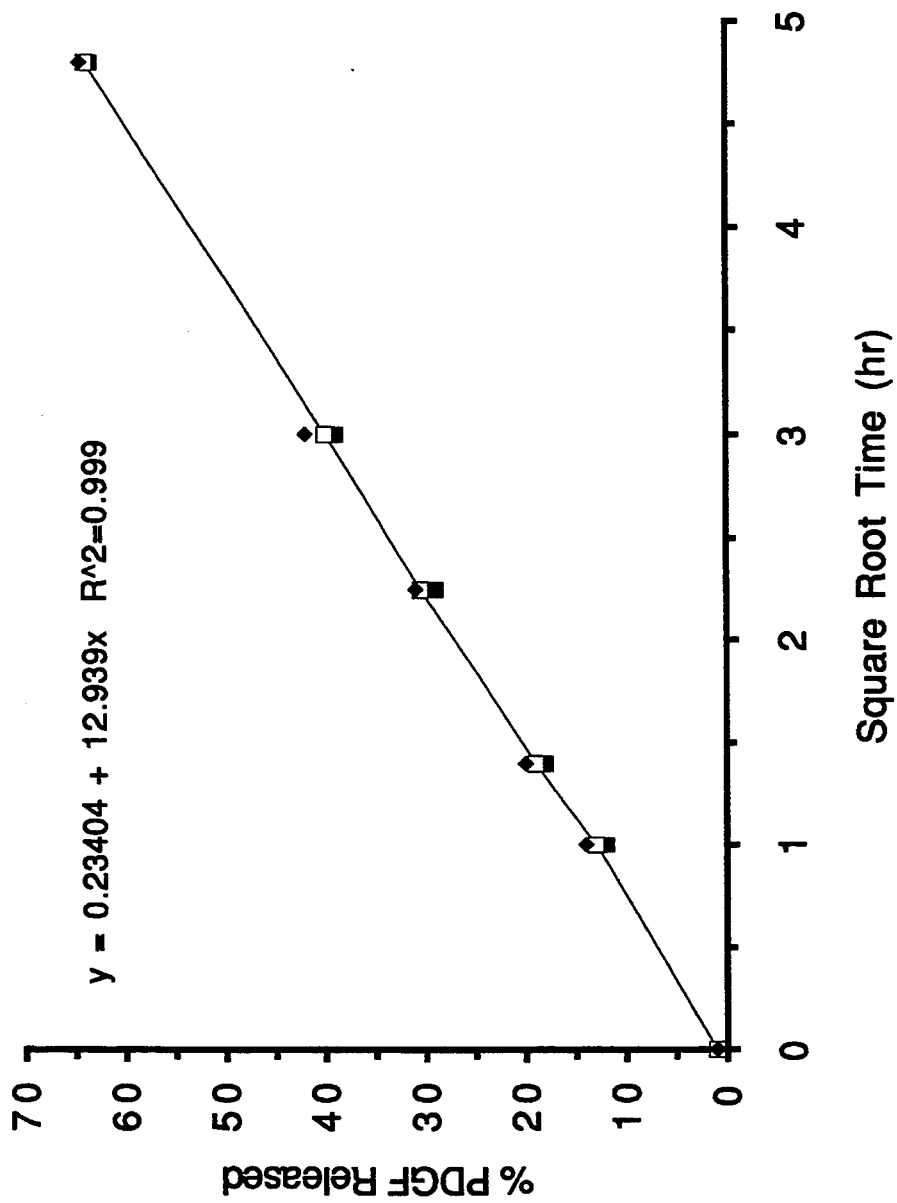
FIG. 5 shows a release profile for PDGF from a wet Gelfoam-Collagen Sponge in vitro showing first order kinetics.
Figure 6:
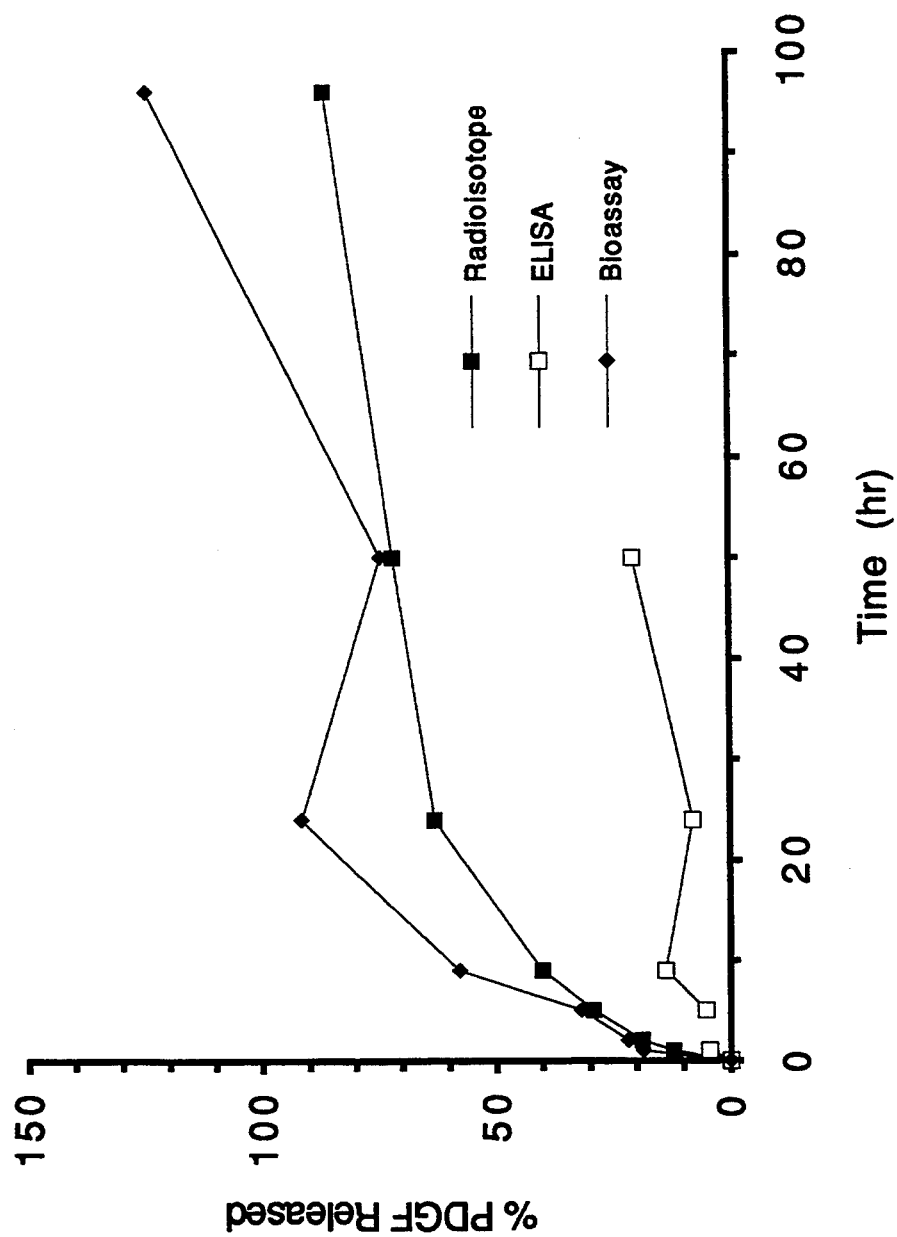
FIG. 6 shows the correlation of PDGF release as measured by a radioisotope, ELISA and PDGF bioassay.

The measurements of release rates of active ingredients from collagen-containing sponges were conducted using Coster Transwell Cells ("Cell") (Costar Co., Cambridge, Mass.) as follows. Collagen-containing sponges with $^{125}$I-PDGF were produced as described in Example 1, and wafers (1.6 cm diameter) were cut from the films. Each wafer was transferred to a Coster Transwell Cell and placed on top of the polycarbonate membrane. 2.5 ml of the receiver solution (water and 1% bovine serum albumin, or water and 0.25% human serum albumin) was added to the Cell holder. The Cells were set on the solution, and the release study was initiated. At specified times, 20 $\mu l$ of the receiver solution was pipetted out and the same amount of fresh solution was replaced in the receiver solution. The sampling procedure was repeated to get another 20 $\mu l$ sample. The radioactivity of the sample was measured with a gamma counter (Beckman Instruments, Co., Irvine, Calif.). The concentration of protein in the receiver solution at any given time was calculated based on the radioactivity and confirmed using other methods such as ELISA and $^3$H-thymidine uptake bioassays. FIGS. 1 and 2 and 4 and 5 show a typical release profile of PDGF from the wafers. The release profile from the dry gel (FIGS. 1 and 2) system was very similar to that of the wet gel (FIGS. 4 and 5) system where the release study was performed immediately after the absorption of the collagen solution by the gelatin sponge. About 80% of the growth factor was released in 100 hours. Data shown in FIGS. 3 and 6 indicate that the drying process does not change the activity of the growth factor.

Figure 7:
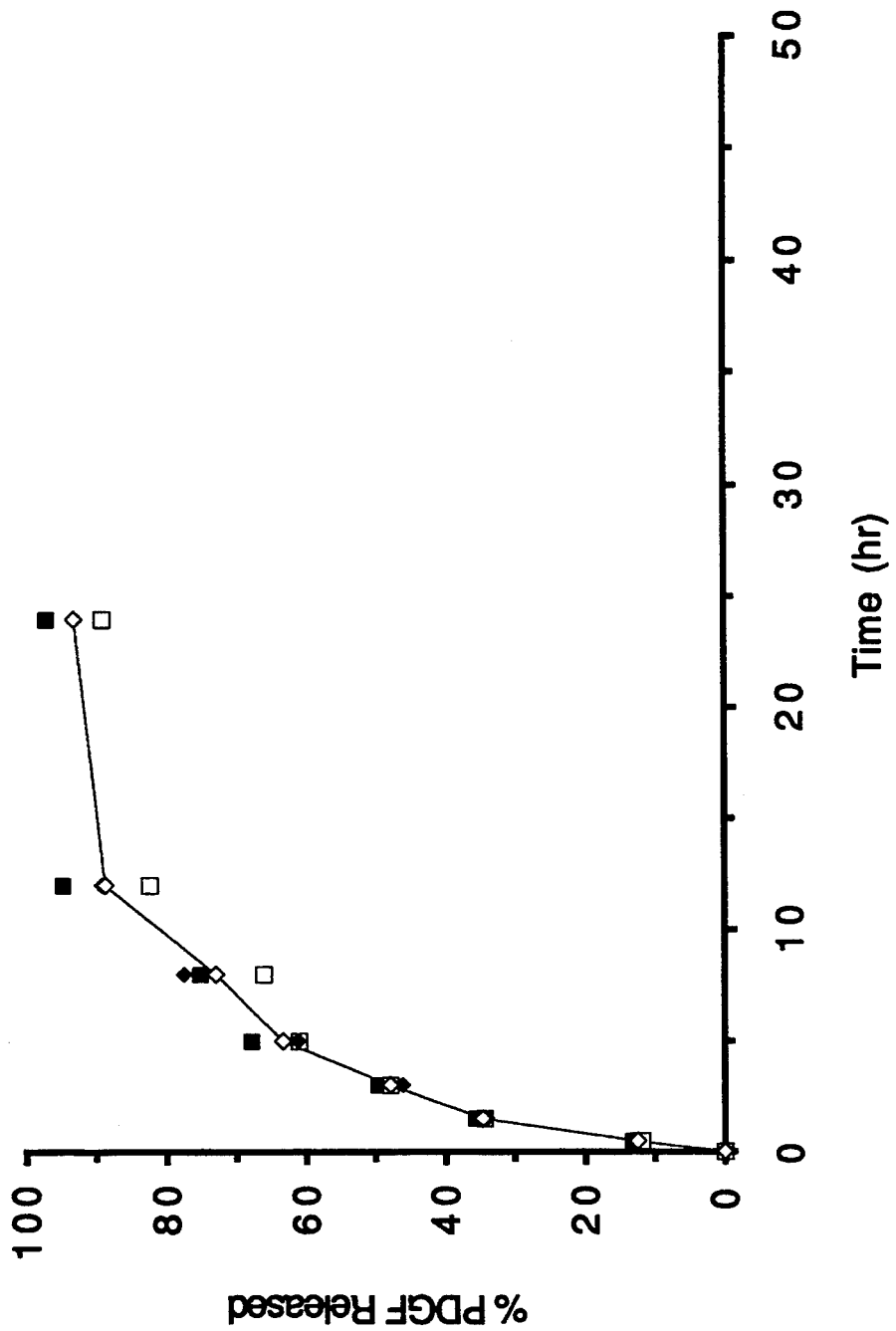
FIG. 7 shows a release profile in vitro for PDGF from a Gelfoam Sponge without the presence of Collagen.

FIG. 7 shows the release of PDGF from a Gelfoam sponge without the presence of collagen. In this study the release of PDGF from the Gelfoam was performed. To remove air bubbles trapped inside the membrane while soaking the membrane (thickness: 1 cm) in PDGF solution, the membrane was soaked in water at reduced pressure. The water soaked membrane was equilibrated in PDGF solution. The release rate of PDGF was measured with Costar Transwell cells using $^{125}$I-PDGF. The release rate was very fast. Most of the PDGF was released in 12 hours. The results obtained from this study show the combination system of collagen-Gelfoam provides for a steady, continuous and sustained release of therapeutic agents over an extended period of time.

EXAMPLE 3

Measurement Of the In Vivo Release Rate of Protein From the Collagen-containing Sponge System.

A. Pre-operative Preparation

Young adult New Zealand White rabbits, weighing approximately 3.0 to 3.5 kg each (M & K Rabbitry, Bentonville, Ark.) were anesthetized using Rompum ® (Farbenfabriken, Bayer, West Germany) as a sedative, followed (10 minutes later) by ketamine (60 mg/kg) and xylaine (5 mg/kg), both administered intramuscularly. Each rabbit's weight was measured and recorded. A small cotton or gauze plug was inserted into both ears of each rabbit, after which the inner surface and outer edges of both ears were shaved using an animal clipper (#40 blade). Commercially available Neet ® depilatory cream was then applied to the inner surface of each ear for 10 minutes, after which time it was removed with dry gauze. The inner surface of each ear was wiped with saline-soaked gauze followed by application of a 70% alcohol solution. The dermis of the inner surface on one ear of each rabbit was blanched by infiltration of the ear with a 2% xylocaine solution containing 1:1000 epinephrine (this requires 1.5 to 3.0 mls total volume) using a 30 gauge needle. The infiltrated area was then scrubbed with 3 cycles of betadine followed by the 70% alcohol solution. Where necessary, the ear plugs were replaced with dry plugs at this point.

The rabbits were then transferred to a sterile surgical room. The blanched ear was immobilized on a plexiglass "ear board" (Washington University Medical Center, Division of Technical Services, St. Louis, Mo.) which utilizes two bar clamps, one at the tip and one at the base of the animal's ear, to stabilize the rabbit ear without compromising its blood supply. The animal was draped, and the surgical field (i.e., the inner surface of the blanched ear) sprayed with Betadine and allowed to dry for 3 to 5 minutes.

B. Wounding

Sterile technique was employed throughout the wounding procedure. Using microsurgical instruments, a 6 mm trephine, and a binocular microscope (10x, Zeiss), the surface of the inner ear of each rabbit was scored gently with a 6 mm biopsy punch, and the biopsy site cleared of all tissue and fibers (including the periosreal membrane) down to the level of bare cartilage, using micro-surgical forceps, tenotomy scissors, a blunt edged 2 mm Lempert periosreal elevator, and sterile cotton-tipped applicators. Perichondrium and overlying tissues were removed by dissection. Biopsies in which the cartilage was completely cut through by the punch were not used for experimental purposes. However, partial thickness scores of the cartilage were considered acceptable. The location of any nicks or natural holes in the cartilage was carefully noted and recorded (for reference on the harvest day). Blood was removed from the biopsy site with sterile, cotton-tipped applicators, with care taken to avoid excess blood in the wound. Each completed biopsy was covered with a small piece of saline-soaked gauze. Four viable 6 mm biopsy ulcers were placed on each wounded ear, two on each side of the midline (as defined by the fold in the ear when it was stabilized upon the board). In any event, no more than 5 total biopsies were placed on each ear. The biopsies were positioned a minimum of 1 cm apart.

Upon completion of one ear, the ear was covered with saline-moistened gauze and then taped shut around the gauze to retain moisture until application of PDGF. The second ear was then blanched, scrubbed, immobilized and wounded in the manner as the first ear. Blood was removed from the biopsy site of each second ear, and each completed biopsy was covered with a small piece of saline-soaked gauze. Upon completion of the second ear, it was covered with saline-moistened gauze until application of PDGF. Any rabbit that showed evidence of recovery from anesthesia at any time prior to this point in the procedure was reanesthetized with 25 mg/kg ketamine, administered intramuscularly.

C. Application Of Active Ingredient to Wounds

Wafers prepared by the procedure of Example I were used for in vivo drug release study. Small wafers (diameter: 5 mm) were used for this experiment. Each wafer was inserted in a wound site (diameter: 6 mm) and a piece of Tagaderm ® was used to make sure that the wafer remained in the wound site.

The rabbits were allowed to recover from anesthesia under the observation of the investigator performing the surgery. Upon recovery, a plastic neck collar (Canine Center, St. Louis, Mo.) extending approximately 15 to 25 cm outward was placed around each rabbit's neck to prevent the rabbit from disrupting the wounds or dressings. The rabbits were returned to an isolation cage where they were maintained until harvest.

Figure 8:
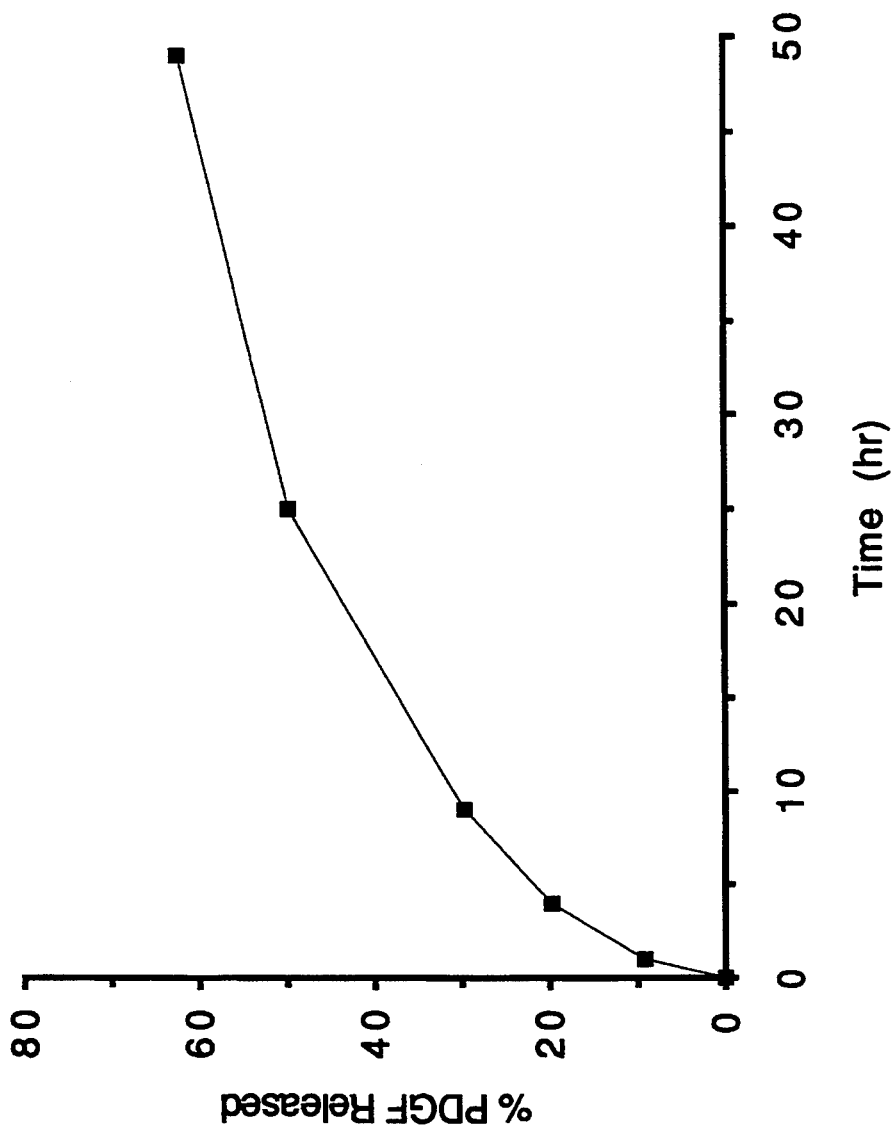
FIG. 8 shows a release profile in vivo for PDGF from a Gelfoam-collagen system prepared with 1% collagen solution.
Figure 9:
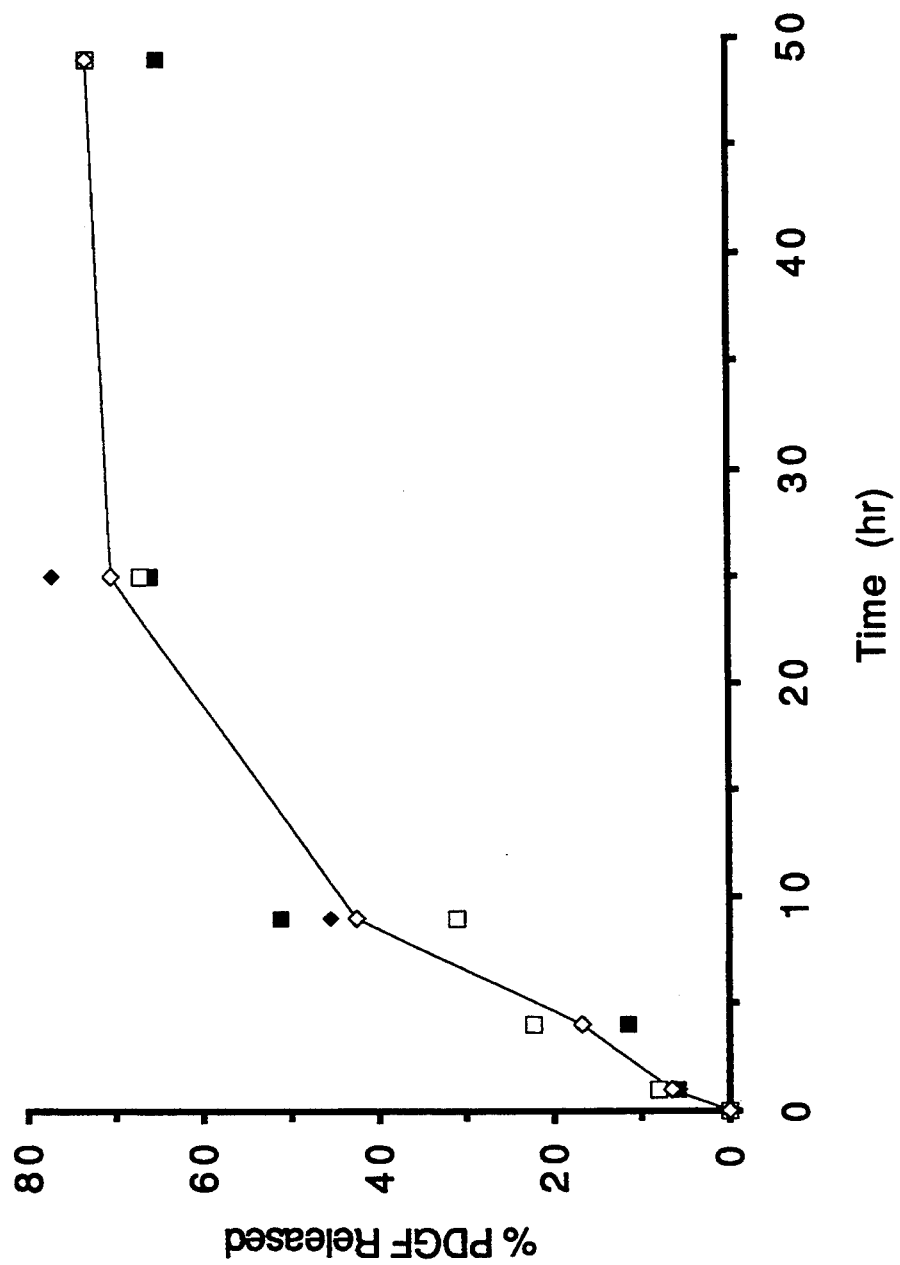
FIG. 9 shows a release profile in vivo for PDGF from a Gelfoam-collagen system prepared with 8% collagen solution.

D. Measurement of the Protein Release from the Collagen-containing Gelatin Sponge System At selected times, several wafers were taken from the wound sites. New pieces of Tagaderm ® were used to cover the wound sites where the wafers were removed. The wafers were collected in test tubes. When all the wafers were recovered, the radioactivity of each wafer was counted. The amount of PDGF released at a given time was calculated from the radioactivity of the remaining wafer. FIG. 8 shows the release profile of PDGF from the collagen-Gelfoam system which was prepared with 1% collagen solution. After 49 hours, about 62% of PDGF was released. FIG. 9 shows the release profile of PDGF from the collagen-Gelfoam system which was prepared with 8% collagen solution. This solution was obtained by dissolving the soluble collagen in distilled water at 60° C. About 73% of PDGF was released after 49 hours.

EXAMPLE 4

Effect of Collagen-Containing Sponges on New Tissue Growth as Measured by the Rat Blood Bundle Model In 30 Lewis rats (125–150 grams), the left tibialis posterior and its parent femoral arterio-venous bundle were dissected from the ankle up to the inguinal ligament. The bundles were sandwiched between two collagen disks 1.6 cm in diameter and placed inside a spoon-shaped silastic mold. Disks from Group A were based on collagen-Gelfoam system. Each disk in the group contained about 125 µg of PDGF. Disks from Group B were based on soluble collagen. Each disk in the group contained about 125 µg of PDGF. Disks from Group C were made of soluble collagen without any PDGF and therefore were used as controls. All the animals were sacrificed at day 30. The contents of the molds were examined grossly and, with a digitizing computer and 3-D reconstruction, were examined histomorphometrically to determine the volume of tissue generated.

Figure 10:
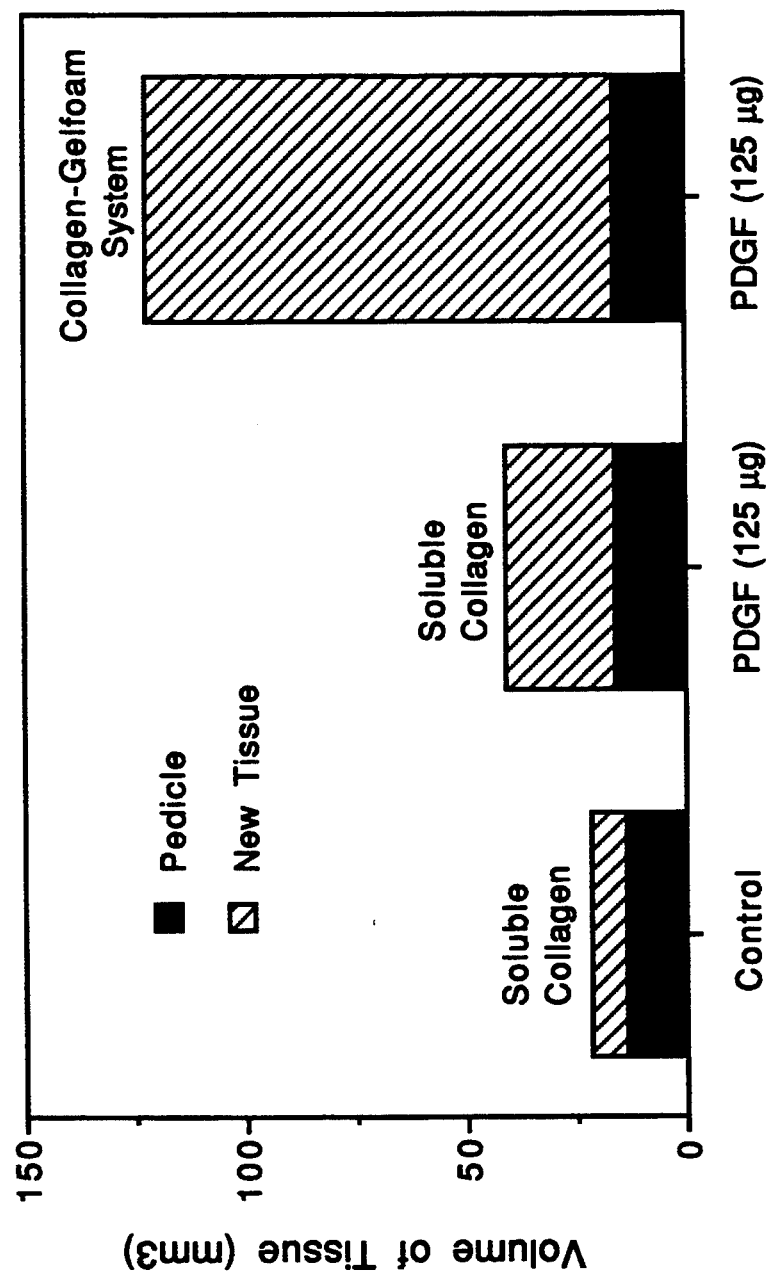
FIG. 10 shows experimental results obtained by using the rat blood bundle model. de

FIG. 10 shows the generation of new tissue volumes of three different groups. A substantial increase in new tissue volume was observed in the animals treated with the collagen-Gelfoam system containing 125 µg of PDGF. In the previous experiments using a soluble collagen system with the same animal model, it was found that wafers based on soluble collagen containing PDGF increased the volume of new tissue significantly after implantation between day 10 and day 15. This was especially evident with high doses of PDGF (120 µg/wafer). The study also showed that 30 days after implantation, the new tissue regressed. The current experiments demonstrate that the collagen-Gelfoam system works well for the generation and/or maintenance of new tissue volume for several weeks.

What is claimed is:

1. A collagen-containing sponge comprising an absorbable, cross-linked gelatin sponge, soluble collagen, and a therapeutically effective amount of an active ingredient.

2. A collagen-containing sponge according to claim 1 wherein said absorbable gelatin sponge is a crosslinked gelatin.

3. A collagen-containing sponge according to claim 2 further comprising a plasticizer.

4. A collagen-containing sponge according to claim 3 wherein said plasticizer is selected from polyethylene glycol and glycerol.

5. A collagen-containing sponge according to claim 3 further comprising a stabilizing agent.

6. A collagen-containing sponge according to claim 5 wherein said stabilizing agent is a sugar selected from the group consisting of mannitol, lactose and glucose.

7. A collagen-containing sponge according to claim 5 further comprising a drying enhancer.

8. A collagen-containing sponge according to claim 7 wherein said drying enhancer is an alcohol selected from the group consisting of ethanol, methanol and isopropyl alcohol.

9. A collagen-containing sponge according to claim 7 further comprising a buffer.

10. A collagen-containing sponge according to claim 1 wherein said active ingredient is selected from the group consisting of PDGF, EGF, FGF, PDEGF, PD-ECGF, KGF, IGF-1, IGF-2, TNF, BDNF, CNTF, and NT-3.

11. A collagen-containing sponge according to claim 9 wherein said active ingredient is selected from the group consisting of PDGF, EGF, FGF, PDEGF, PD-ECGF, KGF, IGF-1, IGF-2, TNF, BDNF, CNTF, and NT-3.

12. A collagen-containing sponge according to claim 10 wherein said active ingredient is KGF.

13. A collagen-containing sponge according to claim 11 wherein said active ingredient is KGF.

* * * * *